US006730105B2

(12) United States Patent
Shiber

(10) Patent No.: US 6,730,105 B2
(45) Date of Patent: May 4, 2004

(54) CLOVER LEAF SHAPED TUBULAR MEDICAL DEVICE

(76) Inventor: Samuel Shiber, 365 Kearney Cir., Manchester, NH (US) 03104

(*) Notice: Subject to any disclaimer, the term of this patent is extended or adjusted under 35 U.S.C. 154(b) by 97 days.

(21) Appl. No.: 10/172,036

(22) Filed: Jun. 14, 2002

(65) Prior Publication Data

US 2002/0151924 A1 Oct. 17, 2002

Related U.S. Application Data

(63) Continuation-in-part of application No. 09/643,181, filed on Aug. 21, 2000, now Pat. No. 6,440,148, which is a continuation-in-part of application No. 09/286,218, filed on Apr. 5, 1999, now Pat. No. 6,106,538, which is a continuation-in-part of application No. 08/904,972, filed on Aug. 1, 1997, now abandoned, which is a continuation-in-part of application No. 08/516,772, filed on Aug. 18, 1995, now Pat. No. 5,653,696, which is a continuation-in-part of application No. 08/107,453, filed on Aug. 17, 1993, now Pat. No. 5,443,443, which is a continuation-in-part of application No. 07/913,231, filed on Jul. 14, 1992, now Pat. No. 5,334,211, which is a continuation-in-part of application No. 07/662,558, filed on Feb. 28, 1991, now Pat. No. 5,306,244, which is a continuation-in-part of application No. 07/499,726, filed on Mar. 27, 1990, now Pat. No. 5,135,531, which is a continuation-in-part of application No. 07/350,020, filed on May 12, 1989, now Pat. No. 4,979,939, which is a continuation-in-part of application No. 07/326,967, filed on Mar. 22, 1989, now Pat. No. 4,957,482, and a continuation-in-part of application No. 07/324,616, filed on Mar. 16, 1989, now Pat. No. 5,007,896, and a continuation-in-part of application No. 07/323,328, filed on Mar. 13, 1989, now Pat. No. 5,002,553, and a continuation-in-part of application No. 07/322,497, filed on Mar. 13, 1989, now Pat. No. 5,024,651, said application No. 07/326,967, said application No. 07/324,616, said application No. 07/323,328, said application No. 07/322,497, each is a continuation-in-part of application No. 90/003,608, filed on Oct. 19, 1994, and a continuation-in-part of application No. 07/286,509, filed on Dec. 19, 1988, now Pat. No. 4,894,051, and a continuation-in-part of application No. 07/243,900, filed on Sep. 13, 1988, now Pat. No. 4,886,490, and a continuation-in-part of application No. 07/225,880, filed on Jul. 29, 1988, now Pat. No. 4,842,579, and a continuation-in-part of application No. 07/205,479, filed on Jun. 13, 1988, now Pat. No. 4,883,458.

(51) Int. Cl.$^7$ ................................................ A61B 17/22
(52) U.S. Cl. .................. 606/159; 606/170; 604/103.07; 604/103.08
(58) Field of Search ................................ 606/159, 194, 606/192, 193, 195, 170; 604/103.08, 103.09, 103.07

(56) References Cited

U.S. PATENT DOCUMENTS

| | | | |
|---|---|---|---|
| 2,078,686 | A | 4/1937 | Rowe |
| 4,273,128 | A | 6/1981 | Lary |
| 4,796,629 | A | 1/1989 | Grayzel |
| 5,196,024 | A | 3/1993 | Barath |
| 5,320,634 | A | 6/1994 | Vigil |
| 5,456,666 | A | 10/1995 | Campbell |
| 5,549,553 | A | 8/1996 | Resselmann |
| 5,609,574 | A | 3/1997 | Kaplan |
| 5,616,149 | A | 4/1997 | Barath |
| 5,628,746 | A | 5/1997 | Clayman |
| 5,713,913 | A | 2/1998 | Lary |
| 5,766,203 | A | 6/1998 | Imran |
| 5,797,935 | A | 8/1998 | Barath |
| 6,013,055 | A | 1/2000 | Bampos |
| 6,306,151 | B1 | 10/2001 | Lary |

Primary Examiner—Michael J. Milano
Assistant Examiner—D. Jacob Davis
(74) Attorney, Agent, or Firm—Samuel Shiber

(57) ABSTRACT

A hydraulically expandable medical device for insertion into an obstruction in a blood vessel, comprising a hydraulically expandable tube having a clover leaf shape in its relaxed, deflated, position; and longitudinal ridges attached to the expandable tube and harbored in the clover leaf shape, the expandable tube adapted to be inflated and expanded with fluid, thereby pushing the elongated ridges outwardly into the obstruction material.

32 Claims, 7 Drawing Sheets

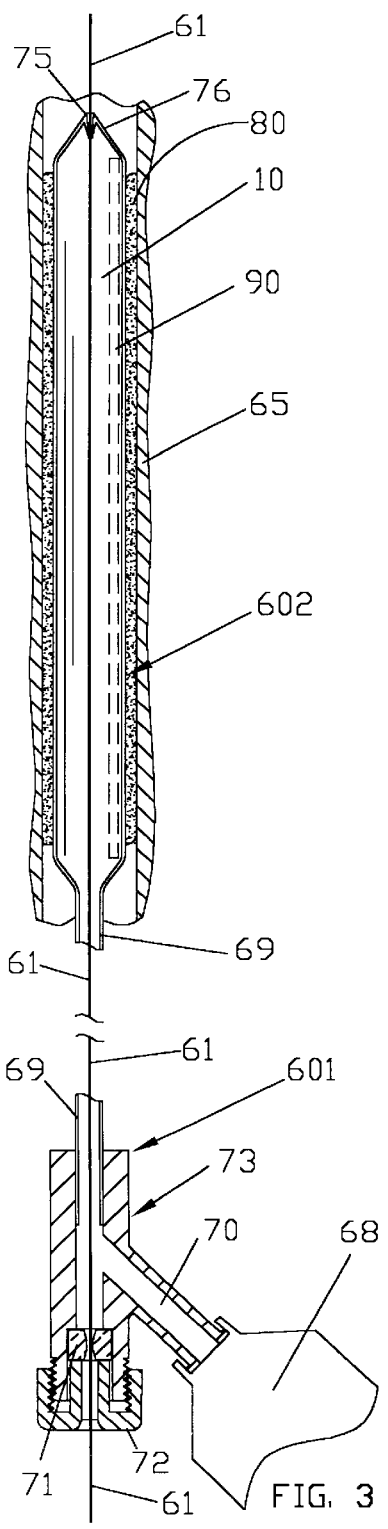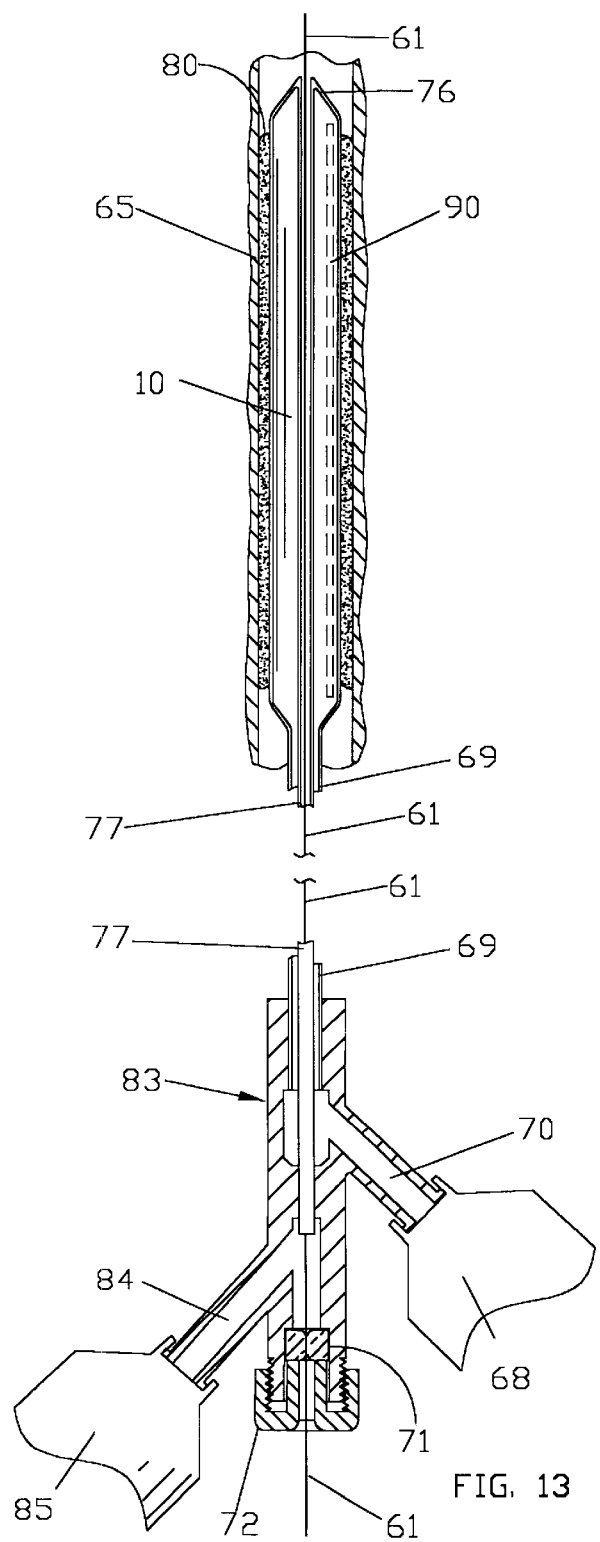

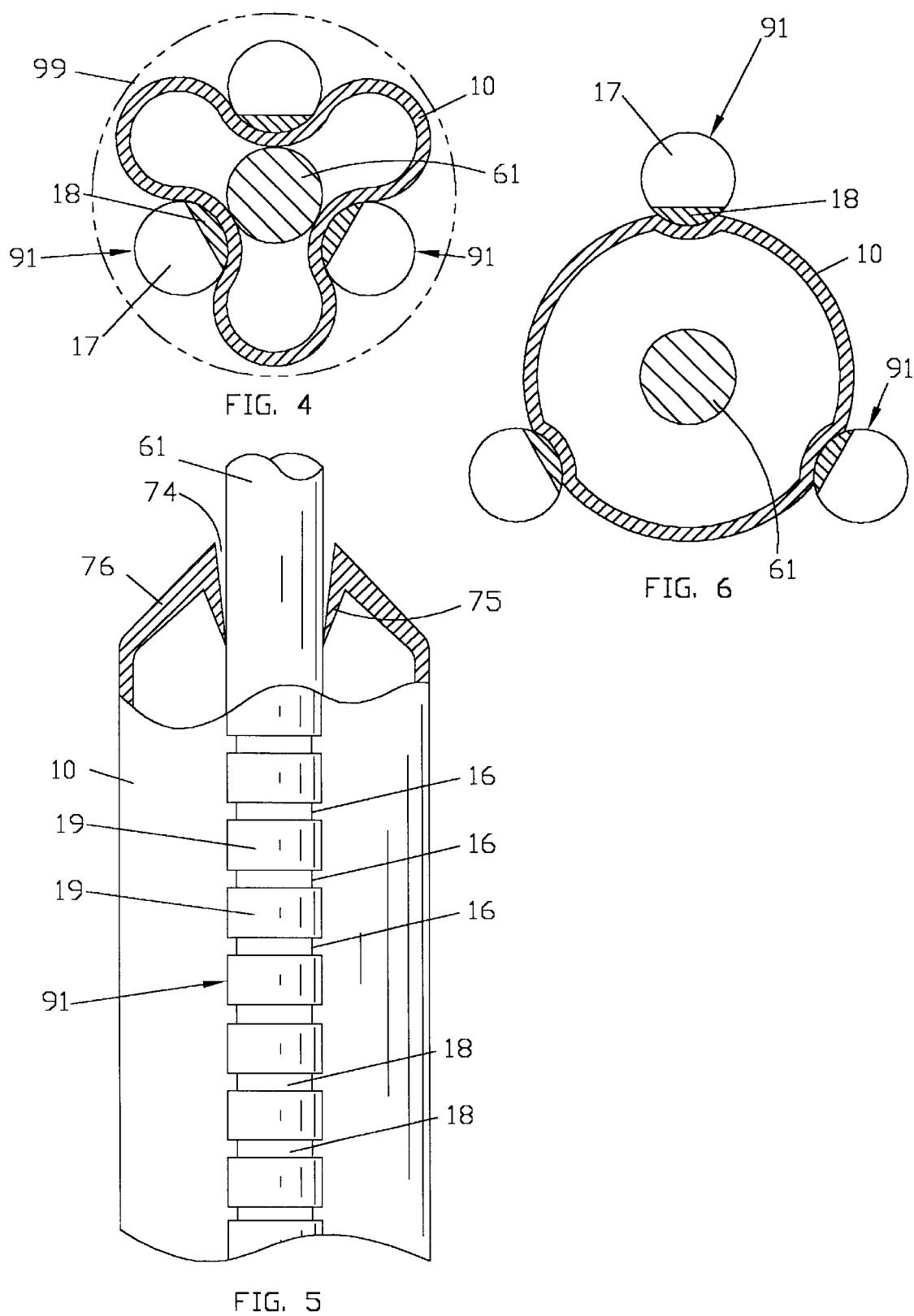

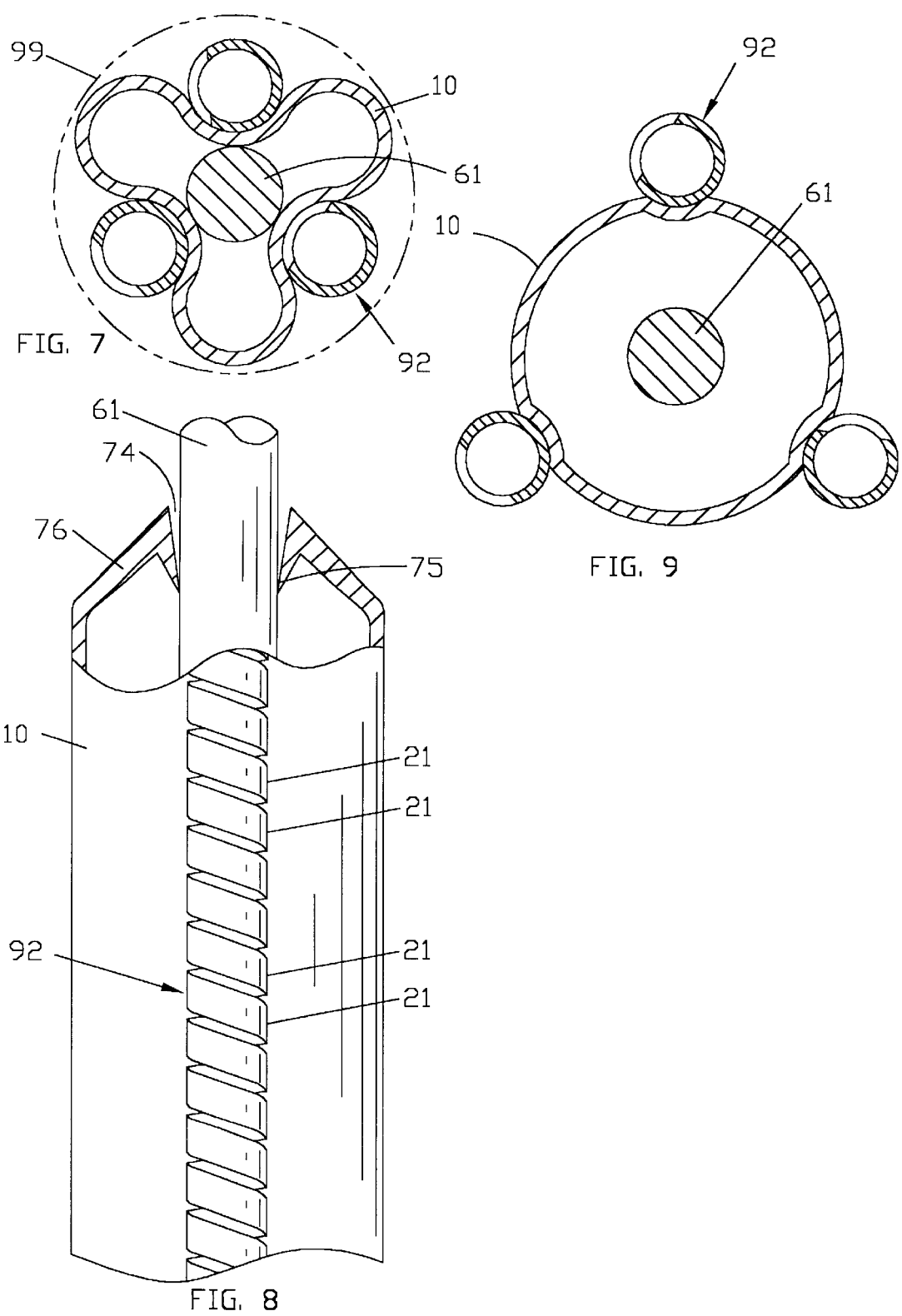

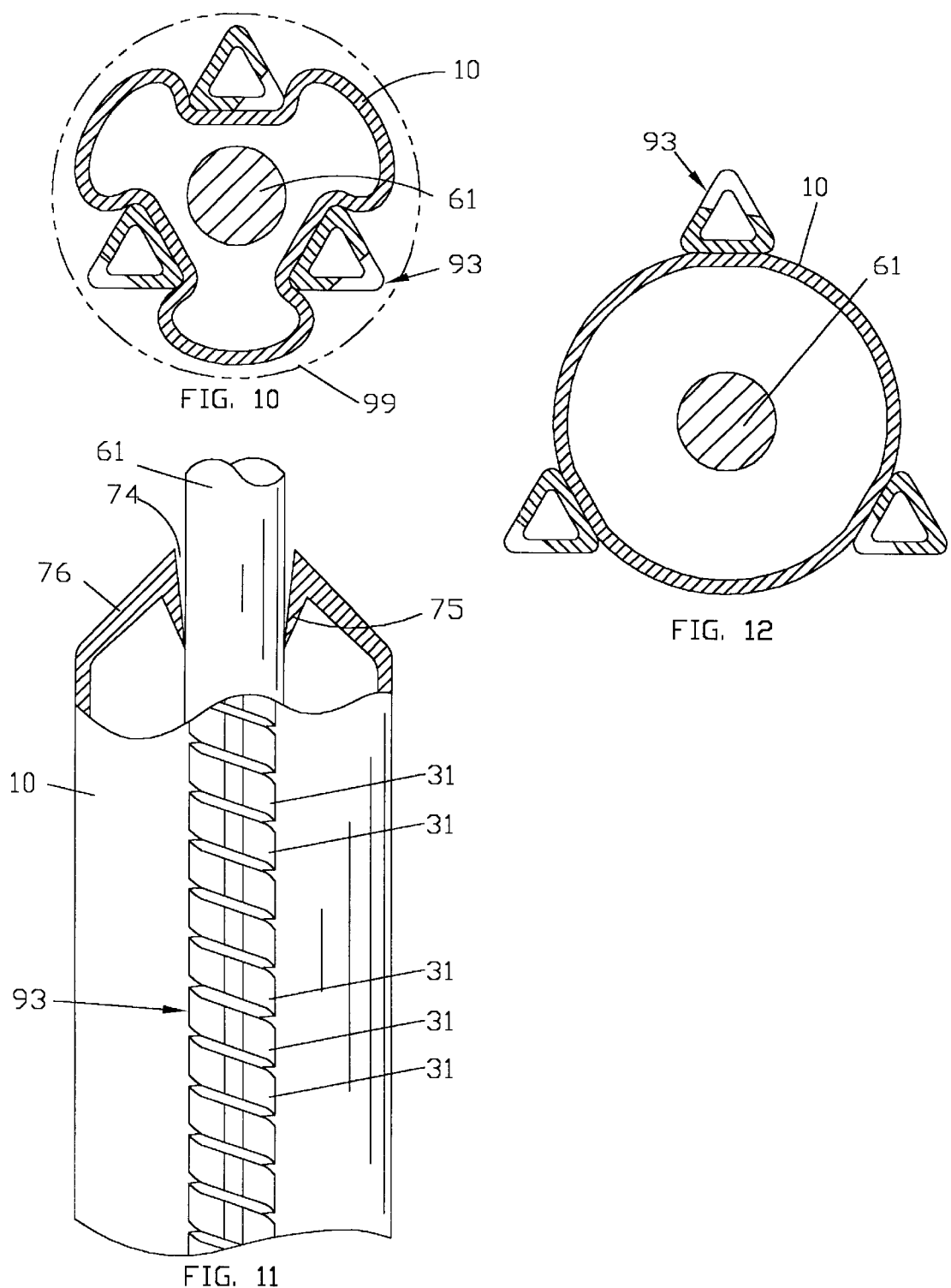

CLOVER LEAF SHAPED TUBULAR MEDICAL DEVICE

CROSS-REFERENCE TO OTHER APPLICATIONS

This application is a continuation in part (CIP) of co-pending application Ser. No. 09/643,181 filed Aug. 21, 2000 (CT20 now U.S. Pat. No. 6,440,148 issued on Aug. 27, 2002) which is a CIP of application Ser. No. 09/286,218 filed Apr. 5, 1999 (CT19 now U.S. Pat. No. 6,106,538 issued on Aug. 22, 2000) which is a CIP of application Ser. No. 08/904,972 filed Aug. 1, 1997 (CT18 abandoned) which is a CIP of application Ser. No. 08/516,772 filed Aug. 18, 1995 (CT17 now U.S. Pat. No. 5,653,696 issued on Aug. 5, 1997) which is a CIP of application Ser. No. 08/107,453 filed Aug. 17, 1993 (CT16 now U.S. Pat. No. 5,443,443 issued on Aug. 22, 1995) which is a CIP of application Ser. No. 07/913,231 filed Jul. 14, 1992 (CT15 now U.S. Pat. No. 5,334,211 issued on Aug. 2, 1994) which is a CIP of application Ser. No. 07/662,558 filed Feb. 28, 1991 (CT14 now U.S. Pat. No. 5,306,244 issued on Apr. 26, 1994) which is a CIP of application Ser. No. 07/499,726 filed Mar. 27, 1990 (CT13 now U.S. Pat. No. 5,135,531 issued on Aug. 4, 1992) which is a CIP of application Ser. No. 07/350,020 filed May 12, 1989 (CT12 now U.S. Pat. No. 4,979,939 issued on Dec. 25, 1990) which is a CIP of four applications: application Ser. No. 07/326,967 filed Mar. 22, 1989 (CT11 now U.S. Pat. No. 4,957,482 issued on Sep. 18, 1990), application Ser. No. 07/324,616 filed Mar. 16, 1989 (CT10 now U.S. Pat. No. 5,007,896 issued on Apr. 16, 1991), application Ser. No. 07/323,328 filed Mar. 13, 1989 (CT9 now U.S. Pat. No. 5,002,553 issued on Mar. 26, 1991) and application Ser. No. 07/322,497 filed Mar. 13, 1989 (CT8 now U.S. Pat. No. 5,024,651). These four applications are CIPs of application Ser. No. 07/286,509 filed Dec. 19, 1988 (CT7 now U.S. Pat. No. 4,894,051 issued on Jan. 26, 1990) which is a CIP of application Ser. No. 07/243,900 filed Sep. 13, 1988 (CT6 now U.S. Pat. No. 4,886,490 issued on Dec. 12, 1989), which is a CIP of three applications: application Ser. No. 07/225,880 filed Jul. 29, 1988 (CT5 now U.S. Pat. No. 4,842,579 issued on Jan. 27, 1989) including Reexamination Request Ser. No. 90/003,608 filed Oct. 19, 1994 (now Reexamination Certificate 2711th issued on Oct. 31, 1995), application Ser. No. 07/205,479 filed Jun. 13, 1988 (CT4 now U.S. Pat. No. 4,883,458 issued on Nov. 28, 1989), all of the above are being incorporated herein by reference.

BACKGROUND AND OBJECTIVES OF THE INVENTION

With age, a large percentage of the population develops atherosclerotic arterial obstructions resulting in diminished blood circulation. The disturbance to blood flow that these obstructions cause may induce blood clots which further diminish or block the blood flow. When this process occurs in the coronary arteries it is referred to as a heart attack. Presently such obstructions are circumvented by surgically grafting a bypass or they are treated by a catheter equipped with a hydraulically expandable tubular element (balloon), made from a non-stretchable thin plastic material which is inserted through the arterial system, over a flexible guide-wire, into the obstruction and then inflated to expand the obstruction's lumen. Some of the problems with balloon catheters are that they tend to tear the arterial wall in an uncontrolled manner along a line of least resistance (which is often a less diseased side of the artery since arterial disease is rarely symmetrical as viewed in an arterial cross section). In extreme cases such uncontrolled tearing of the artery can progress through all the layers of the arterial wall cracking it open and causing an internal bleeding.

An objective of the present invention is to provide an improved hydraulically expandable catheter for insertion into the obstruction which is made of a hydraulically expandable tube that generally has a clover leaf shape in its relaxed, deflated, position. The expandable tube has longitudinal ridges attached to it that are harbored in the folds of the clover leaf shape and, when the expandable tube is inflated to become substantially circular, the ridges part the obstruction material along multiple lines as they are displaced radially outward and are pushed into the material.

A further objective is to prepare the obstruction site for a follow-up treatment with an atherectomy system (as shown for example in my cross-referenced parent applications) or for placing a stent (as shown for example in U.S. Pat. No. 4,503,569 issued on Mar. 12, 1985 or U.S. Pat. No. 4,886,062 issued on Dec. 12, 1989).

A further objective is to provide a ridge made of a series of interconnected elements so that it is flexibly bendable (along its longitudinal axis) but still has a rigid cross section that will not cave-in when pushed into the surrounding obstruction material.

A further objective is to provide a ridge having a parting edge that is pointed away from the obstruction material when the expandable tube is in its relaxed, deflated, position. This makes the catheter less likely to cause any damage while it is advanced, or retracted, from the obstruction site while maximizing the effectiveness of the edge as it is pushed into the obstruction material. When the expandable tube is inflated, the change in the expandable tube's cross section from a clover leaf shape to a substantially circular shape is utilized to turn the edge towards the obstruction material.

A further objective is to provide a ridge having a parting edge that is recessed in the ridge and less likely to contact the expandable tube when the expandable tube is in its relaxed position. This also makes the parting edge less likely to cause any damage to the vasculature or to soft parts of the catheter while it is advanced, or retracted, from the obstruction site. When the expandable tube is inflated, the change in the expandable tube's cross section from a clover-leaf shape to a substantially circular shape is utilized to bring the parting edge out of the ridge towards the obstruction material.

BRIEF DESCRIPTION OF THE FIGURES

FIG. 4 shows a cross sectional end view of a first embodiment of the present invention with a clover leaf shaped expandable tube in its relaxed, deflated, position and round longitudinal ridges, made of plastic rods, harbored in folds of the expandable tube, FIG. 5 shows a partial cross sectional side view of the distal end of the embodiment of FIG. 4, FIG. 6 shows a cross sectional end view of the embodiment of FIG. 4, with expandable tube inflated and expanded to a substantially circular shape, thereby the elongated ridges outwardly, FIG. 7 shows a cross sectional end view of a catheter, according to a second embodiment of the present invention, with a clover leaf shaped expandable tube in its relaxed, deflated, position and round longitudinal ridges, made of spiral wire, harbored in folds of the clover leaf shaped expandable tube, FIG. 8 shows a partial cross sectional side view of the embodiment of FIG. 7, FIG. 9 shows a cross sectional end view of a catheter of FIG. 7, with the expandable tube inflated and expanded to a substantially circular shape thereby pushing the elongated ridges outwardly, FIG. 10 shows a cross sectional end view of a third embodiment of the present invention with a clover leaf shaped expandable tube in its relaxed, deflated, position and triangular longitudinal ridges, made of spiral wire, harbored in folds of the clover leaf shape expandable tube, FIG. 11 shows a partial cross sectional side view of the embodiment of FIG. 10, FIG. 12 shows a cross sectional end view of the embodiment of FIG. 10, with the expandable tube inflated and expanded to a substantially circular shape thereby pushing the elongated ridges outwardly, FIG. 13 schematically shows a distal and proximal sections of a catheter, incorporating a guidewire shield, as in the fourth and fifth embodiments.

DETAILED DESCRIPTION OF THE DRAWINGS

Figure 1:
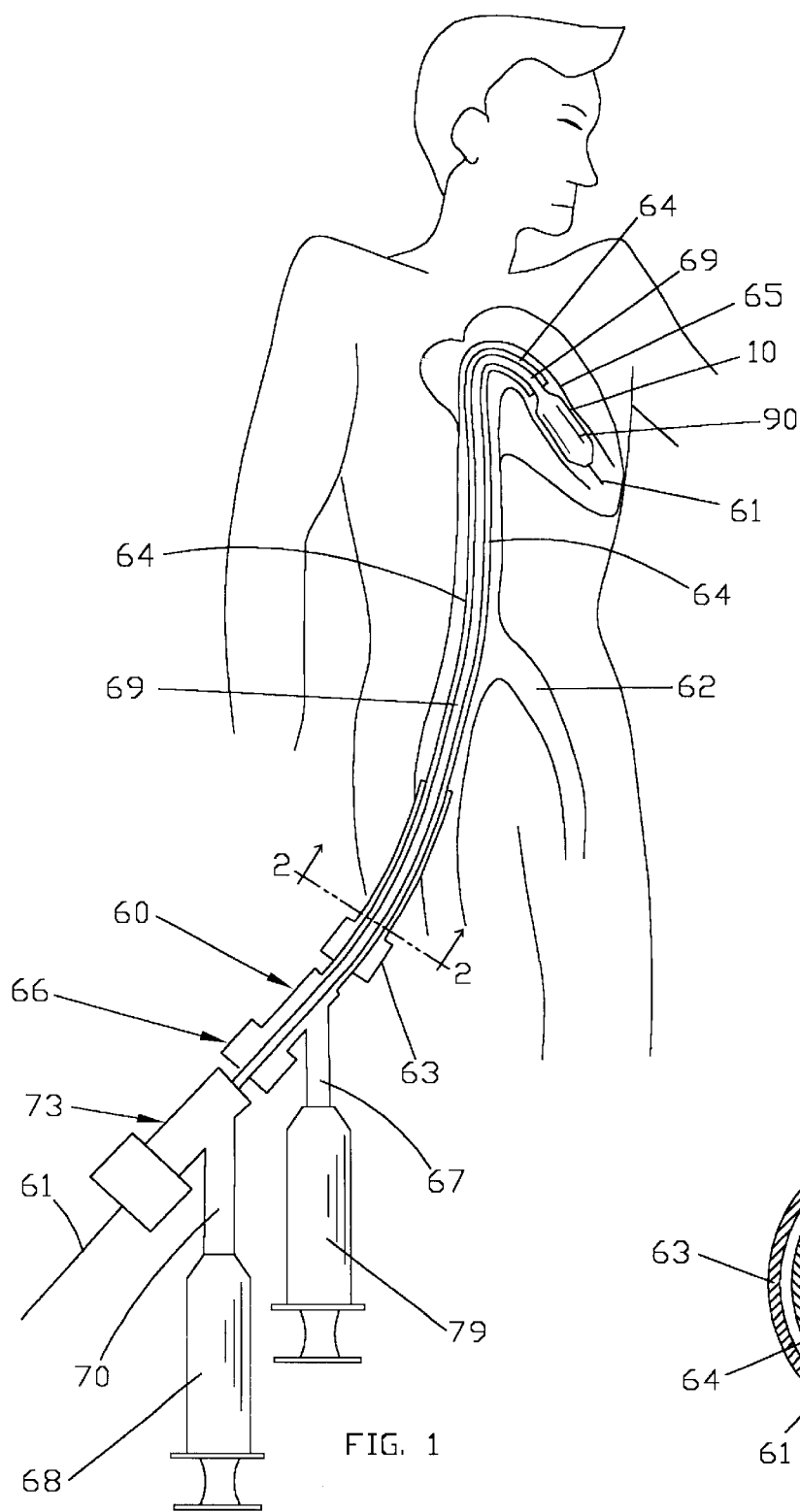
FIG. 1 schematically shows a general side view of a catheter, according to the present invention, inserted at the groin area through the vasculature of a patient into an obstructed coronary artery ("side view" indicates a FIG. that is viewed generally in a perpendicular direction to the longitudinal axis of the catheter whereas "end view" is viewed along the longitudinal axis)
Figure 2:
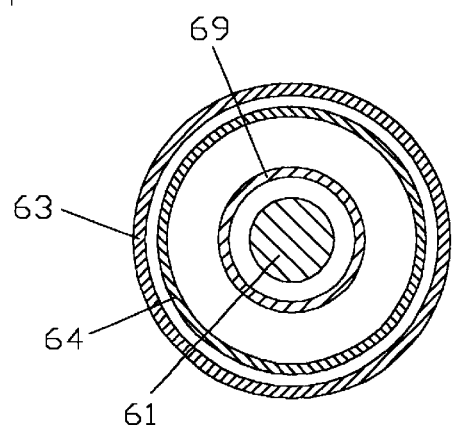
FIG. 2 shows a cross section of the catheter of FIG. 1 along line 2—2 marked on FIG. 1, FIG. 3 schematically shows a cross sectional side view of a distal and proximal sections of a catheter as in the first, second and third embodiments.
Figure 14:
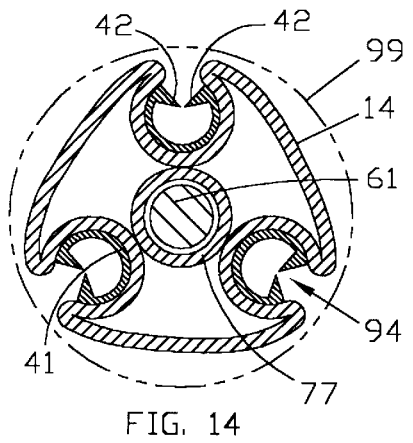
FIG. 14 shows a cross sectional end view of a fourth embodiment of the present invention with a clover leaf shaped expandable tube in its relaxed, deflated, position and ridges harbored in folds of the clover leaf shape expandable tube, the ridges having parting edges that, in this view, are pointed away from the obstruction material.

FIG. 1 schematically shows a catheter 60, according to the present invention. The catheter is conventionally inserted over a guidewire 61 into a vasculature 62 of a patient, through an introducer 63 and a guiding catheter 64. The guiding catheter 64 leads the catheter 60 through the vasculature into an obstructed coronary artery 65. A proximal end of the guiding catheter is equipped with a Touhy Borst type hemostatic seal body 66 having a side port 67 through which fluid (e.g., radio-opaque fluid) can be introduced into the guiding catheter and injected through it into the artery by means of a syringe 79. FIG. 2 shows a cross section of the catheter of FIG. 1 along line 2—2 marked on FIG. 1 (guidewires, introducers, guiding catheters, angioplasty catheters, Touhy Borst hemostatic seal bodies and syringes are commercially available from various companies, e.g., Cordis Corp., Miami, Fla.; Guidant Corp., Indianapolis, Ind.; Medtronic Corp., Minneapolis, Minn.; Qosina Corp., Edgewood, N.Y.). The term "vasculature" refers to a patient's blood vessels. The term "distal" indicates closeness to the end of a guidewire or of a catheter that is inserted into the vasculature whereas "proximal" indicates closeness to the other end that remains out of the vasculature.

FIG. 3 shows the proximal and distal sections 601 and 602, respectively, of the catheter. The distal section comprises a hydraulically expandable tube 10 with longitudinal ridges 90 that are attached to the expandable tube and are harbored in the clover leaf shape of the expandable tube, between its folds. Referring back also to FIGS. 1 and 2, the expandable tube 10 is hydraulically connected to an inflation device, in the form of a syringe 68, through a flexible conduit 69 and a Touhy Borst type hemostatic seal body 73 which connects the conduit to a side port 70 to which the syringe 68 is also connected. A hemostatic seal 71 and a screw-on cap 72 which are a part of the hemostatic seal body 73 adjustably compress the seal (note FIG. 3). As the screw-on cap 72 is tightened it compresses the seal 71 against the guidewire 61 to minimize leakage between them or it can be loosened to make for an easier sliding of the guidewire through the seal. The syringe 68 is used to inflate the expandable tube 10, preferably with a radio-opaque fluid, and conversely to deflate it.

The hydraulically expandable tube 10 has a clover leaf shape in its relaxed, deflated, position that harbors the elongated ridges (note FIGS. 4, 7 and 10). As a result of the inflation the expandable tube tends to assume a circular shape (which is less than a perfect circle due to the ridges that are bonded to it) and thereby radially pushes the elongated ridges outwardly into an obstruction material 80 that obstructs the artery 65, parting and expanding it.

The expandable tube is preferably made from a non stretching material of the type that is used in conventional angioplasty expandable tubes (e.g., Nylon, Polyethylene-Terephthalate, Urethane) to prevent the inflated expandable tube from over stretching beyond a certain diameter and thereby preventing it from over stretching the blood vessel that it is expanding.

The ridges 90 are longitudinally flexible to allow the expandable tube, to which they are attached, to bend as the expandable tube is advanced through the vasculature. However, they have a rigid cross section to enable them to be pushed and to penetrate into the surrounding obstruction material. Additionally, the ridges' cross section is preferably shaped so that the ridges' initial contact with the surrounding material is along a narrow line, to ease the ridges' penetration into the surrounding obstruction material. For example, a first embodiment of the invention, shown in FIGS. 4 to 6, utilizes a design iteration of the ridges 91 in the form of plastic (e.g., Nylon) rods with a round cross section. Such a circular cross section would contact a surrounding obstruction material (schematically represented in FIG. 4 and also in FIGS. 7, 10, 14 and 18 by the circular phantom line 99) along a narrow line, as will be understood by those skilled in the art. To enhance the ridges' longitudinal flexibility (i.e., bendability), the ridges 91 are divided into a series of interconnected elements 19 by multiple cuts 16 along the length of the ridge. Each cut extends through most of the cross sectional area 17 while the remaining un-cut portion of the cross sectional area 18 acts as a flexible link that interconnects the elements 19. A second embodiment, shown in FIGS. 7 to 9, utilizes a second design iteration of the ridges 92 in the form of a flat wire wound to a spiral. The spiral has a round cross section as shown in FIGS. 7 and 9, and each coil 21 of the spiral acts as an element of the ridge. A third embodiment, shown in FIGS. 10 to 12, an expandable tube 10 and a third design iteration of the ridges 93 that are also made of flat wire wound to a spiral and each coil 31 of the spiral acts as an element of the ridge. However, the ridge 93, and coils 31, have a triangular cross section that further narrows the ridges' initial line of contact with the surrounding obstruction material 99 and stiffens the ridges' cross section as will be understood by those skilled in the art.

Referring back to FIGS. 1, 3 and 13, the catheter 60 is preferably advanced through the vasculature over a conventional guidewire 61 (to which I referred to, in my parent application Ser. No. 07/350,020, as a "pilot wire"). The guidewire can be disposed directly in the expandable tube and in the conduit as in the first three embodiments (note FIGS. 3, 5, 8 and 11) and extend through an opening 74 that is surrounded by a lip seal 75 that is attached to an otherwise closed distal end 76 of the expandable tube. As the guidewire is slid through and engages the lip seal 75 it closes the opening 74 and thereby enables the pressurization and inflation of the expandable tube 10. Alternatively, the guidewire 61 can be disposed in a shield 77 that isolates the guidewire from the fluid that flows in conduit 69, as shown in FIG. 13 and in the fourth and fifth embodiments shown in FIGS. 14 to 21. The distal end of the shield is attached to the distal end of the expandable tube 76 (in place of the opening 74 and lip seal 75 that were present in the first three embodiments) and at its proximal end the shield is affixed in a modified hemostatic seal body 83 and is connected to a second side port 84 (note FIG. 13) which can be used to flush and inject fluid through the shield (e.g., solution containing radio-opaque material, anticoagulants or medications) using a syringe 85. While this design iteration may be less prone to leakage of pressurized fluid it tends to be slightly less compact.

Figure 16:
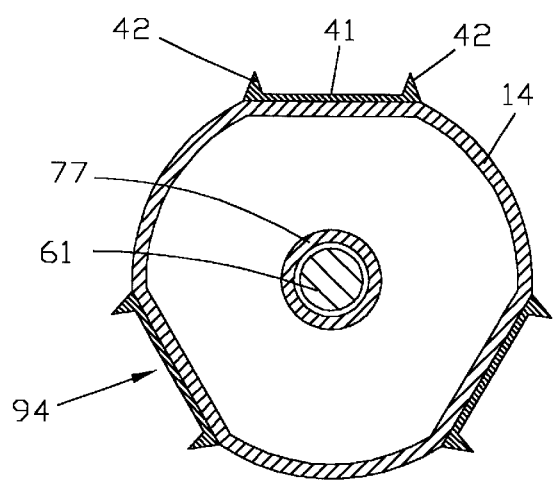
FIG. 16 shows a cross sectional end view of the embodiment of FIG. 14, with the expandable tube inflated and expanded to a substantially circular shape thereby pushing the elongated ridges outwardly while causing the parting edges to turn outwardly.
Figure 15:
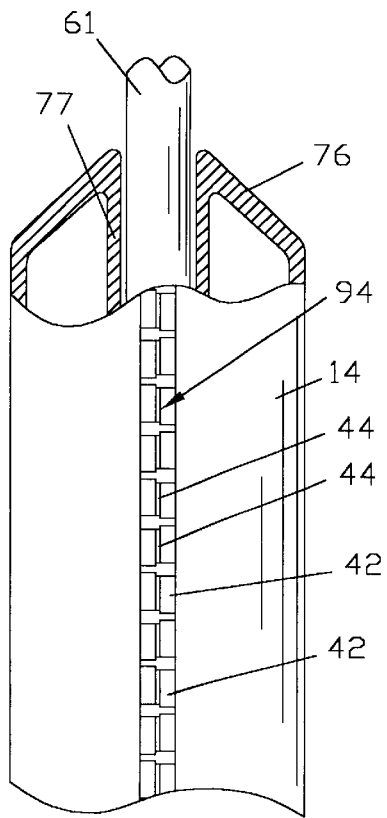
FIG. 15 shows a partial cross sectional side view of the embodiment of FIG. 14.
Figure 17:
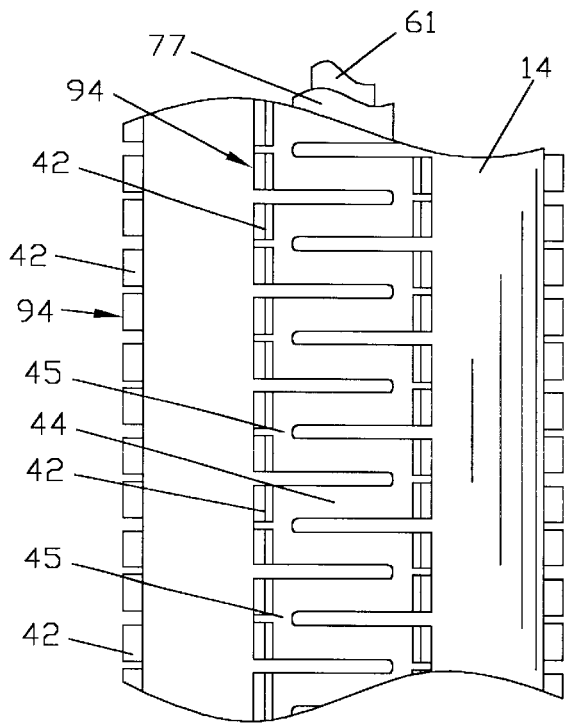
FIG. 17 shows a side view of what is shown in HG 16.
Figure 18:
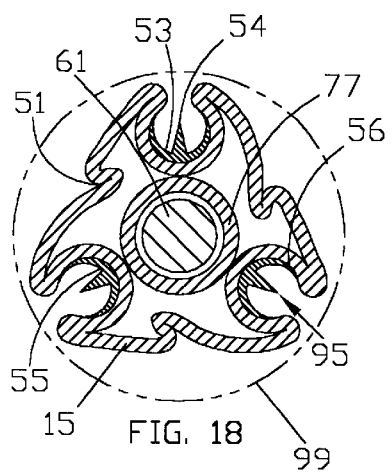
FIG. 18 shows a cross sectional end view of a fifth embodiment of the present invention with an enlarged clover leaf shaped expandable tube in its relaxed, deflated, position and ridges harbored in folds of the expandable tube, the ridges having retracted parting edges at their mid section.

FIGS. 14 to 17 show a fourth embodiment that utilizes a clover leaf shaped expandable tube 14 and ridges 94 that comprise a flexible arch 41 that is bonded to the expandable tube 14. The ridges 94 have parting edges 42 that are pointed away from the obstruction material, when the expandable tube and arch are in their relaxed positions (note FIG. 14). This reduces the likelihood of the expandable tube or vasculature being damaged by the parting edges during introduction, advancement or withdrawal of the catheter through the vasculature. As the expandable tube 14 is inflated the arches 41 are elastically deformed, as illustrated in FIG. 16, and as a result the parting edges are turned outwardly towards the surrounding obstruction material. The arch and parting edge can be fabricated in one piece from, for example, metal (e.g., stainless steel shape memory alloys), or the arch and parting edge can be fabricated separately and attached to one another. To increase the longitudinal flexibility of the ridge 94 it can be made of elements 44 (note FIG. 17) that are connected with narrow linking sections 45. Thus the resulting parting edge 42 creates a series of short cuts in the obstruction material along which the obstructing material preferentially parts. Upon deflation the flexible arch 41 urges the expandable tube to return to its clover leaf shape. While the ridge 94 is shown with a parting edge at each of its ends, optionally, additional ridges can be attached to the arch or a single ridge can be attached to an arch as illustrated in the next embodiment.

Figure 20:
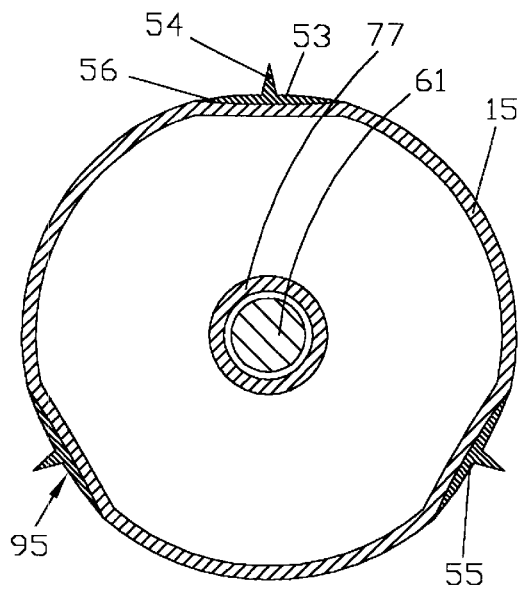
FIG. 20 shows a cross sectional end view of the embodiment of FI(. 18, with the expandable tube inflated and expanded to a substantially circular shape thereby pushing the elongated ridges outwardly while causing the parting edges to also move outwardly, and, FIG. 21 shows a side view of what is shown in FIG. 20.
Figure 19:
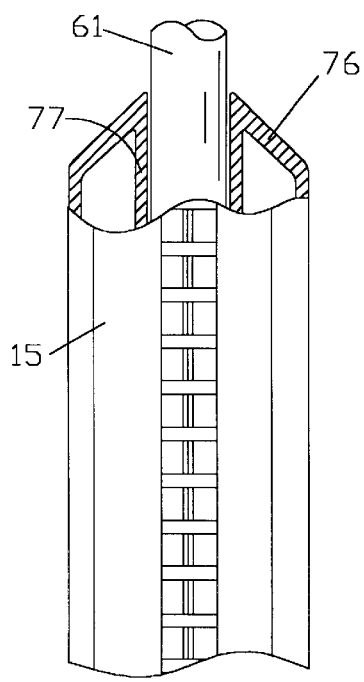
FIG. 19 shows a partial cross sectional side view of the embodiment of FIG. 18.
Figure 21:
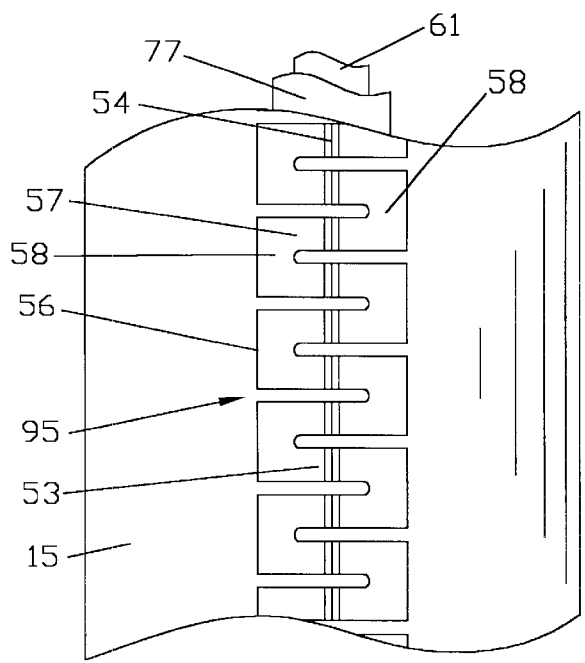

FIGS. 18 to 21 show a fifth embodiment with a clover leaf shaped expandable tube 15 with pleats 51 that increase the expanded tube's diameter (note FIG. 20). This embodiment utilizes ridges 95 comprising an arch 53 that is bonded to the expandable tube 15. A parting edge 54 is attached to a mid section of the ridge so that when the expandable tube and the ridge are in their relaxed position the parting edge is retracted inwardly in the arch (note FIG. 18) This shields the un-inflated tube 15 and blood vessel from the parting edge and reduces the likelihood of the expandable tube or vasculate being damaged by the parting edge during introduction and advancement or withdrawal of the catheter in the vasculature. As the expandable tube is inflated and expanded the parting edge moves out of the arch (note FIG. 20) to part the surrounding obstruction.

The mid section of the arch 55 is thicker (note FIGS. 18 and 20) to better support the parting edge 54 and the ends 56 are thinner to lessen the peeling forces that develop and tend to separate the arch from the expandable tube when the expandable tube is inflated. To increase the longitudinal flexibility the ridge 95 can be made of elements 57 (note FIG. 21) that are connected with narrow linking sections 58 that are formed near the thinner part 56 of the arch. As in the previous embodiment, the parting edges 54 create a series of short cuts in the obstruction material along which the obstructing material preferentially parts.

A method of treating a patient with an obstructed blood vessel with a hydraulically expandable medical device, according to the present invention, that in its relaxed position has a clover leaf shaped tubular body with longitudinal ridges attached to and harbored in the clover leaf shape, comprises the steps of inserting the medical device into the obstructed blood vessel and inflating and expanding the tubular body, thereby pushing the ridges into the obstruction material.

It should be understood that, as with standard angioplasty procedures, the use of a guiding catheter is not always called for (e.g., when treating peripheral arteries) nor is the use of an introducer always called for (e.g., when accessing the vasculature surgically).

Additionally, it should be understood that the features taught in connection with one embodiment can be used with features taught in connection with another embodiment (e.g., the non-shielded guidewire design that is illustrated in the first three embodiments can be used together with the ridges shown in the last two embodiment, or the ridges of the first three embodiments can be mounted on the expandable tubes shown in the last two embodiments).

Further, while the embodiments have been illustrated with expandable tubes that have three ridge-harboring-folds and a cross section generally resembling a three leaflet clover leaf, it should be understood that expandable tubes with a modified number or shape of leaflets that, in their relaxed deflated position can harbor the ridges, can be used, and that such expandable tubes and other design variations can be made to the embodiments and the methods described in the specification without departing from the spirit of the invention or the scope of the claims.

I claim:

1. A hydraulically expandable medical device for insertion into an obstruction in a blood vessel, comprising:

a hydraulically expandable tube having a clover leaf shape in its relaxed position; and longitudinal ridges attached to said expandable tube and harbored in said clover leaf shape;

said expandable tube adapted to be inflated and expended with fluid, thereby pushing said elongated ridges outwardly into the obstruction material.

2. As in claim 1, wherein said expandable tube is made from a non stretching material.

3. As in claim 1, wherein at least one of said ridges is longitudinally flexible and has a rigid cross section.

4. As in claim 1, wherein at least one of said ridges comprises a series of linked elements.

5. As in claim 1, wherein at least one of said ridges is made of a spiral wire.

6. As in claim 1, wherein at least one of said ridges is made of a flat spiral wire.

7. As in claim 1, wherein at least one of said ridges has a cross section so that said ridge initially contacts the surrounding obstruction material along a narrow line.

8. As in claim 7, wherein at least one of said ridges has a substantially circular cross section.

9. As in claim 7, wherein at least one of said ridges has a substantially triangular cross section.

10. As in claim 1, wherein at least one of said ridges has at least one parting edge that is pointed away from the obstruction material when said expandable tube is in its relaxed position and is turned towards the surrounding obstruction material as the expandable tube is inflated.

11. As in claim 1, wherein at least one of said ridges comprises an arch having a parting edge attached to at least one of its ends at an angle so that it is pointing in the general direction of the center of the arch when said expandable tube is in its relaxed position and is turned towards the surrounding obstruction material as the expandable tube is inflated.

12. As in claim 11, wherein said arch is bonded to said expandable tube and acts as a return spring, urging said expandable tube to return to its clover leaf shape when it is deflated.

13. As in claim 1, wherein at least one of said ridges is bonded to said expandable tube and acts as a return spring, urging said expandable tube to return to its clover leaf shape when it is deflated at least one of said ridges having a parting edge attached to its mid section so that when said expendable tube and at least one of said ridges are in their relaxed position said parting edge is retracted inwardly in said arch and when said expandable tube is inflated and expanded said parting edge moves outwardly of said arch.

14. As in claim 13, wherein at least one of said ridges has a thickened mid section.

15. A hydraulically expandable medical device for insertion into an obstruction in a blood vessel over a guidewire, comprising:

a hydraulically expandable tube having a clover leaf shape in its relaxed position; and longitudinal ridges attached to said expandable tube and harbored in said clover leaf shape;

said expandable tube adapted to be inflated and expanded with fluid to become substantially circular, thereby pushing said elongated ridges outwardly into the obstruction.

16. As in claim 15, wherein said expandable tube is made from a non stretching material.

17. As in claim 15, wherein at least one of said ridges is longitudinally flexible and has a rigid cross section.

18. As in claim 15, wherein at least one of said ridges comprises a series of linked elements.

19. As in claim 15, wherein at least one of said ridges is made of a spiral wire.

20. As in claim 15, wherein at least one of said ridges is made of a flat spiral wire.

21. As in claim 15, wherein at least one of said ridges has a cross section so that said ridge initially contacts the surrounding obstruction material along a narrow line.

22. As in claim 21, wherein at least one of said ridges has a substantially circular cross section.

23. As in claim 21, wherein at least one of said ridges has a substantially triangular cross section.

24. As in claim 15, wherein at least one of said ridges has at least one parting edge that is pointed away from the obstruction material when said expandable tube is in its relaxed position and is turned towards the surrounding obstruction material as the expandable tube is inflated.

25. As in claim 15, wherein at least one of said ridges comprises an arch having a parting edge attached to at least one of its ends at an angle so that it is pointing in the general direction of the center of the arch when said expandable tube is in its relaxed position and is turned towards the surrounding obstruction material as the expandable tube is inflated.

26. As in claim 25, wherein said arch is bonded to said expandable tube and acts as a return spring, urging said expandable tube to return to its clover leaf shape when it is deflated.

27. As in claim 15, wherein at least one of said ridges is bonded to said expandable tube and acts as a return spring, urging said expandable tube to return to its clover leaf shape when it is deflated, said ridge having a parting edge attached to its mid section so that when said expandable tube and said ridge are in their relaxed position said parting edge is retracted inwardly in said arch and when said expandable tube is inflated and expanded said parting edge moves outwardly of said arch.

28. As in claim 27, wherein at least one of said ridges has a thickened mid section.

29. A method of treating a patient with an obstructed blood vessel with a hydraulically expandable medical device having, in its relaxed position, a clover leaf shaped tubular body with longitudinal ridges attached to said expandable tube and harbored in said clover leaf shape, comprising the following steps:

inserting said medical device into the blood vessel; and inflating said tubular body by introducing fluid into said tubular body thereby pushing said ridges outwardly into the obstruction.

30. A method of treating a patient with an obstructed blood vessel with a hydraulically expandable medical device having, in its relaxed position, a clover leaf shaped tubular body with longitudinal ridges attached to said expandable tube and harbored in said clover leaf shape, at least one of said ridges having a cross section comprising an arch having a parting edge attached to an end of said arch at an angle so that it is pointing in the general direction of the center of the arch, comprises the following steps: inserting said medical device into said obstructed artery, inflating said tubular body with fluid to expand and turn said cutting edge toward the obstruction material and to push it into the obstruction material.

31. The method of claim 29, wherein said medical device is inserted into said blood vessel over a guidewire.

32. The method of claim 30, wherein said medical device is inserted into said blood vessel over a guidewire.

* * * * *